(12) United States Patent
Maljaars et al.

(10) Patent No.: US 11,834,525 B2
(45) Date of Patent: *Dec. 5, 2023

(54) HETEROPOLYSACCHARIDES

(71) Applicant: DSM IP ASSETS B.V., Heerlen (NL)

(72) Inventors: Cornelia Elizabeth Paulina Maljaars, Echt (NL); Pim Van Hee, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 17/197,476

(22) Filed: Mar. 10, 2021

(65) Prior Publication Data

US 2021/0189015 A1    Jun. 24, 2021

Related U.S. Application Data

(63) Continuation of application No. 17/021,665, filed on Sep. 15, 2020, now abandoned, which is a continuation of application No. 15/034,231, filed as application No. PCT/EP2014/073570 on Nov. 3, 2014, now Pat. No. 11,325,986.

(30) Foreign Application Priority Data

Nov. 5, 2013  (EP) .................................... 13191595

(51) Int. Cl.
| | |
|---|---|
| C08B 3/00 | (2006.01) |
| A23C 9/123 | (2006.01) |
| C08L 5/00 | (2006.01) |
| C12P 19/04 | (2006.01) |
| A23C 9/137 | (2006.01) |
| A23C 19/032 | (2006.01) |
| A23C 19/09 | (2006.01) |
| C12N 1/20 | (2006.01) |
| A23C 9/13 | (2006.01) |
| A23C 19/05 | (2006.01) |
| C12R 1/46 | (2006.01) |
| C08B 37/00 | (2006.01) |

(52) U.S. Cl.
CPC ............ *C08B 37/006* (2013.01); *A23C 9/123* (2013.01); *A23C 9/1238* (2013.01); *A23C 9/1307* (2013.01); *A23C 9/137* (2013.01); *A23C 19/0323* (2013.01); *A23C 19/054* (2013.01); *A23C 19/09* (2013.01); *C08L 5/00* (2013.01); *C12N 1/20* (2013.01); *C12N 1/205* (2021.05); *C12P 19/04* (2013.01); *A23C 2240/00* (2013.01); *A23Y 2240/75* (2013.01); *C12R 2001/46* (2021.05)

(58) Field of Classification Search
CPC ........ C08B 37/006; C12N 1/205; C12N 1/20; A23C 9/123; A23C 9/1238; A23C 9/1307; A23C 9/137; A23C 19/0323; A23C 19/054; A23C 19/09; A23C 2240/00; C08L 5/00; C12P 19/04; C12R 2001/46; A23Y 2240/75
USPC ... 426/40, 34, 36, 42, 43, 49, 580, 582, 583
See application file for complete search history.

(56) References Cited

FOREIGN PATENT DOCUMENTS

WO    2012159922 A1    11/2012

OTHER PUBLICATIONS

F. Vaningelgem et al: "Biodiversity of Exopolysaccharides Produced by *Streptococcus thermophilus* Strains Is Reflected in Their Production and Their Molecular and Functional Characteristics," Applied and Environmental Microbiology, vol. 70, No. 2, Feb. 1, 2004 (Feb. 1, 2004), pp. 900-912, XP55034421.*
Almirn-Riog et al: "The complete cps gene cluster from *Streptococcus thermophilus* NCFB 2393 involved in the biosynthesis of a new exopolysaccharide." Microbiology, vol. 146, No. 11, Nov. 1, 2000 (Nov. 1, 2000), pp. 793-2802, XP55034218.*
De Vuyst L D et al: "Recent developments in the biosynthesis and applications of heteropolysaccharides from lactic acid bacteria," International Dairy Journal, Elsevier Applied Science, Barking, GB, vol. 11, No. 9, Jan. 1, 2001 (Jan. 1, 2001), pp. 687-707, XP002999473.*
Almirn-Roig et al: "The complete cps gene cluster from *Streptococcus thermophilus* NCFB 2393 involved in the biosynthesis of a new exopolysaccharide." Microbiology, vol. 146, No. 11, Nov. 1, 2000 (Nov. 1, 2000), pp. 2793-2802, XP55034218.
International Search Report dated Jan. 13, 2015, issued in PCT/EP2014/073570.
International Preliminary Report on Patentability dated Oct. 19, 2015, issued in PCT/EP2014/073570.
Vaningelgem, Frederik et al., "Biodiversity of Exopolysaccharides Produced by *Streptococcus thermophilus* Strains Is Reflected in Their Production and Their Molecular and Functional Characteristics", Applied and Environmental Microbiology, Feb. 2004, pp. 900-912, vol. 70, No. 2.
Ruas-Madiedo, Patricia et al., "An overview of the functionality of exopolysaccharides produced by lactic acid bacteria", International Dairy Journal, 2002, pp. 163-171, vol. 12.
Ruas-Madiedo, Patricia et al., "Role of exopolysaccharides produced by *Lactococcus lactis* subsp. cremoris on the viscosity of fermented milks", International Dairy Journal, 2002, pp. 689-695, vol. 12.
Ruas-Madiedo, Patricia et al., "Invited Review: Methods for the Screening, Isolation, and Characterization of Exopolysaccharides Produced by Lactic Acid Bacteria", Journal of Dairy Science, 2005, pp. 843-856, vol. 88., No. 3.

(Continued)

*Primary Examiner* — Leslie A Wong
(74) *Attorney, Agent, or Firm* — MCBEE MOORE & VANIK IP, LLC

(57) ABSTRACT

The present invention relates a heteropolysaccharide characterized in that it is substantially composed of the monosaccharides glucose and galactose and rhamnose and N-acetylgalactosamine and a process for the production thereof. The invention further relates to a bacterium capable of producing said heteropolysaccharide and to the use of the heteropolysaccharide and the bacterium for improving the texture of fermented milk products.

9 Claims, No Drawings

(56) References Cited

OTHER PUBLICATIONS

Ruas-Madiedo, Patricia et al., "Biosynthesis and Chemical Composition of Exopolysaccharides Produced by Lactic Acid Bacteria", Bacterial Polysaccharides Current Innovations and Future Trends, Jan. 1, 2009, pp. 279-310.
Ricciardi, A. et al., "Exopolysaccharide production by *Streptococcus thermophilus* SY: production and preliminary characterization of the polymer", Journal of Applied Microbiology, 2002, pp. 297-306, vol. 92.
DSM IP Assets B.V., Demand of PCT/EP2014/073570, Letter to EPO, Sep. 7, 2015.
De Vuyst, L. et al., "Exopolysaccharides from Lactic Acid Bacteria", Elsvier LTD., 2007, pp. 477-519, vol. 2.15.
Van Casteren, Willemiek, "Structural characterisation and enzymic modification of exopolysaccharides from Lactococcus lactis", Wagingen University—Thesis, 2000.
Nwodo, Uchechukwu U. et al., "Bacterial Exopolysaccharides: Functionality and Prospects", International Journal of Molecular Sciences, 2012, pp. 14002-14015, vol. 13.
Almirón-Roig, Eva et al., "The complete cps gene cluster from *Streptococcus thermophilus* NCFB2393 involved in the biosynthesis of a new exopolysaccharide", Microbiology, 2000, pp. 2793-2802, vol. 146.
Zeidan, Ahmad A. et al., "Polysaccharide production by lactic acid bacteria: from genes to industrial applications", FEMS Microbiology Reviews, 2017, pp. 1-33.
Van Casteren, W.H.M et al., "Characterisation and modification of the exopolysaccharide produced by *Lactococcus lactis* subsp. cremoris B40", Carbohydrate Polymers, 1998, pp. 123-130, vol. 37.
Yoo, Seung Min, "Bacterial Polysaccharides: Current Innovations and Future Trends", Biotechnology Journal, 2009, pp. 1091, vol. 4.
Sánchez-Medina, Inmaculada et al., "Structural determination of a neutral exopolysaccharide produced by *Lactobacillus delbrueckii* ssp. bulgaricus LBB.B332", Carbohydrate Research, 2007, pp. 2735-2744, vol. 342.
De Vuyst, L. et al., "Exopolysaccharide-producing *Streptococcus thermophilus* strains as functional starter cultures in the production of fermented milks", International Dairy Journal, 2003, pp. 707-717, vol. 13.
Notice of opposition to a European Patent (EP3066223) dated May 23, 2018.
Opposition against EP3066223 dated Aug. 16, 2019.
Ullrich, Matthias, "Bacterial Polysaccharides: Current Innovations and Future Trends", Biotechnology Journal, 2009, p. 1091.
Oral Proceedings: Opposition against EP 3066223 dated Oct. 16, 2019.
Decision: Oral proceedings of Oct. 16, 2019.

* cited by examiner

HETEROPOLYSACCHARIDES

CROSS-REFERENCE TO RELATED APPLICATIONS

This application is a continuation of U.S. patent application Ser. No. 17/021,665, filed Sep. 15, 2020, now abandoned, which is a continuation of U.S. patent application Ser. No. 15/034,231, filed May 4, 2016, now U.S. Pat. No. 11,325,986, which is a § 371 National Stage Application of PCT/EP2014/073570, filed Nov. 3, 2014, which claims priority to European Patent Application No. 13191595.1, filed Nov. 5, 2013. The disclosure of the priority applications are incorporated in their entirety herein by reference.

FIELD OF THE INVENTION

The present invention relates to heteropolysaccharides, their production by microorganisms and their application in the dairy industry to make fermented milk products.

BACKGROUND OF THE INVENTION

Polymers from plant, animal, and microbial origin play an important role in food formulations. Food polymers are long-chain, high-molecular-mass molecules that dissolve or disperse in water to give texturizing properties. Most of the biopolymers used by the food industry are polysaccharides from crop plants (e.g. starch) or seaweeds (e.g. carrageenan) and animal proteins like caseinate and gelatin. The functional properties of plant carbohydrates in foods are determined by quite subtle structural characteristics. For industrial practice, most are chemically modified.

Alternative biothickeners are the microbial exopolysaccharides. These polymers may be assembled as capsular (CPS) polysaccharides that are tightly associated with the cell surface, or they may be liberated into the growth medium (i.e. "ropy" polysaccharides). The term exopolysaccharide (EPS) may be used to describe either type of extracellular polysaccharide (Broadbent J. R. et al, 2003, Journal Dairy Science, 86, 407-423, *"Biochemistry, genetics and applications of exopolysaccharide production in Streptococcus thermophilus: a review"*).

EPS occur widely among bacteria and microalgae and less among yeasts and fungi. Examples of industrially important microbial EPS are dextrans from *Leuconostoc mesenteroides*, xanthan from *Xanthomonas campestris* and EPS of the gellan family from *Sphingomonas paucimobilis*. These EPS represent only a small fraction of the current biopolymer market. Factors limiting the use of microbial EPS are their economical production, which requires a thorough knowledge of their biosynthesis and an adapted bioprocess technology, the high costs of their recovery, and the non-food bacterial origin of most of them. Strains of generally recognized as safe (GRAS) food grade microorganisms, in particular lactic acid bacteria (LAB) that are able to produce EPS in large enough quantities, are an interesting alternative for food uses of EPS. Moreover, these microorganisms can be used for the in situ production of EPS, particularly for fermented dairy products, to improve their rheology, texture and body, and mouthfeel.

EPS from LAB can be subdivided into two groups, namely homopolysaccharides (HoPS) and heteropolysaccharides (HePS). HoPS are composed of one type of constituting monosaccharides (d-glucopyranose or d-fructofuranose) (Monsan, P., et al., 2001, International Dairy Journal, 11, 673-683, *Homopolysaccharides from lactic acid bacteria.*). HePS are composed of a backbone of repeated subunits, that are branched (at positions C2, C3, C4, or C6) or unbranched and that consist of three to eight monosaccharides, derivatives of monosaccharides or substituted monosaccharides. For recent reviews see Vaningelgem et al. (2004) applied and Environmental Microbiology 70(2), 900-912 *"Biodiversity of Exopolysaccharides Produced by Streptococcus thermophilus Strains Is Reflected in Their Production* and *Their Molecular* and *Functional Characteristics"* and De Vuyst et al. (2001) International Dairy Journal, 11, 687-707. *"Recent developments in the biosynthesis and applications of heteropolysaccharides from lactic acid bacteria".*

Table 1 in de Vuyst et al. (2001) summarizes the HePS of 34 different lactic acid bacteria. The repeating units comprise the following saccharides: glucose (Glc), GlcNAc (N-acetylglucosamine), galactose, (Gal), GalNAc (N-acetyl-galactosamine), rhamnose (Rha) and fucose (Fuc). Table 4 in Vaningelgem et al. summarizes the HePS of 25 different *Streptococcus thermophilus* strains. While de Vuyst (2001) categorized the different EPS on the basis of the number of monosaccharides in the repeating unit, starting with tri-saccharides up to octa-saccharides, Vaningelgem et al. have defined groups I-VI depending on their qualitative monosaccharide composition. For instance, Group I is composed of galactose and glucose while Group V is composed of galactose, glucose, rhamnose and N-acetyl-galactosamine. Additional structures of the repeating units of HePS are summarized in Table 2 of Ruas-Madiedo et al, 2002, International Dairy Journal, 12, 163-171, *An overview of the functionality of exopolysaccharides produced by lactic acid bacteria*

It is generally known that the functionality of the EPS is influenced by the 3D-structure of the molecule (i.e. the so-called hydrodynamic radius—$R^h$). The two main parameters determining the 3D-structure are the molecular mass (MW in Dalton) in combination with the repeating unit of the EPS, which is determined by the monosaccharide composition, type of branching and linkage in the polymer.

EPS's s from LAB's have technological significance in the production of several fermented dairy products. The use of "ropy" starters containing EPS-forming *S. thermophilus* and *Lactobacillus delbrueckii* subsp. *bulgaricus* is a common practice in the production of yoghurt to improve texture, avoiding syneresis and increase the viscosity of the yoghurt. In addition, EPS-producing bacteria are applied to improve the yield, texture and functionality of cheeses, especially that of reduced fat cheeses (see Broadbent J. R. et al, 2003, Journal Dairy Science, 86, 407-423, *"Biochemistry, genetics and applications of exopolysaccharide production in Streptococcus thermophilus: a review"*).

We have now surprisingly found a new type of heteropolysaccharide with excellent texturizing proprieties. The combination of the sugar composition and molecular weight of the heteroploysaccharide has not yet been reported before.

DETAILED DESCRIPTION OF THE INVENTION

In a first aspect the invention provides a heteropolysaccharide which is composed substantially of the monosaccharides glucose, galactose, rhamnose and N-acetylgalactosamine and which has a molecular weight of 100 kDa to 10,000 kDa. Substantially is defined herein that at least 90%, preferably at least 95%, more preferably at least 98% of the heteropolysaccharide is composed of the monosaccharides glucose and galactose and rhamnose and N-acetylgalactosamine, based on dry matter of the heteropolysaccharide. In a preferred embodiment, the heteropolysaccharide is composed of 30-50 mole % glucose, 10-30 mole % galactose, 10-30 mole % rhamnose and 10-30 mole % N-acetylgalactosamine and whereby the total mole % of glucose and galactose and rhamnose and N-acetylgalactosamine is 100%. More preferred the heteropolysaccharide is composed of 35-45 mole % glucose, 15-25 mole % galactose, 15-25 mole % rhamnose and 15-25 mole % N-acetylgalactosamine, preferably whereby the total mole % of glucose and galactose and rhamnose and N-acetylgalactosamine is 100%. In another embodiment the heteropolysaccharide is characterized in that the ratio of the mole % of glucose and the mole % of galactose is between 1.0 and 2.0. The most preferred heteropolysaccharide is composed of 40 mole % glucose, 20 mole % galactose, 20 mole % rhamnose and 20 mole % N-acetyl-galactosamine.

The composition of the heteropolysaccharide according to the invention can be expressed in several ways. The composition can be expressed as weight percentage of the individual monosaccharides or as the mole percentage of the individual monosaccharides. Alternatively, the mole percentage can be expressed as the molar ratio (integer number) of the individual monosaccharides. For example, the most preferred embodiment described above and which is composed of 40 mole % glucose, 20 mole % galactose, 20 mole % rhamnose and 20 mole % N-acetylgalactosamine is then expressed as:

glucose:galactose:rhamnose:N-acetylgalactosamine=2:1:1:1

The heteropolysaccharide of the invention may be composed of a basic repeating unit. The repeating unit may have the same composition as the composition of heteropolysaccharide. Preferably the repeating unit of the heteropolysaccharide of the invention is a pentasaccharide composed of glucose and galactose and rhamnose and N-acetylgalactosamine. A pentasaccharide is defined herein as a saccharide composed of 5 monosaccharides. The pentasaccharide of the present invention preferably has the following composition:

glucose:galactose:rhamnose:N-acetylgalactosamine=2:1:1:1

The heteropolysaccharide of the invention has a molecular weight of 100 to 10,000 kDa. More preferably a molecular weight of 200 kDa to 10,000 kDa, preferably a molecular weight of 300 kDa to 10,000 kDa, preferably a molecular weight of 400 kDa to 10,000 kDa, preferably a molecular weight of 450 kDa to 10,000 kDa, preferably a molecular weight of 500 kDa to 10,000 kDa, more preferably a molecular weight of 200 kDa to 8,000 kDa, preferably a molecular weight of 300 kDa to 6,000 kDa, preferably a molecular weight of 400 kDa to 4,000 kDa, preferably a molecular weight of 450 kDa to 2,000 kDa, most preferably a molecular weight of 500 kDa to 1,500 kDa. The molecular weight of the heteropolysaccharide of the invention is defined herein as an averaged molecular weight. The molecular weight of the heteropolysaccharide will have a distribution of molecular weight around the averaged molecular weight. The averaged molecular weight may be determined by the skilled person by methods known in the art, for instance size exclusion chromatography.

The heteropolysaccharide of the invention may have any of the sugar compositions as described hereinbefore in combination with any of the molecular weight ranges as described hereinbefore. A highly preferred heteropolysaccharide of the invention is composed of 35-45 mole % glucose, 15-25 mole % galactose, 15-25 mole % rhamnose and 15-25 mole % N-acetylgalactosamine and whereby the total mole % of glucose and galactose and rhamnose and N-acetylgalactosamine is 100% and has a molecular weight of 500 kDa to 1,500 kDa. Another highly preferred heteropolysaccharide of the invention has the following sugar composition:

glucose:galactose:rhamnose:N-acetylgalactosamine=2:1:1:1 in combination with a molecular weight of 500 kDa to 1,500 kDa

The advantage of the heteropolysaccharide of the invention is that it has excellent thickening properties in fermented milk products and gives long texture in comparison to heteropolysaccharides which, while being composed of the same monosaccharides glucose, galactose, rhamnose and N-acetylgalactosamine, have a molecular weight which is much smaller than 100 kDa (see example).

In a second aspect, the invention provides a bacterium capable of producing the heteropolysaccharide of the invention. Preferably the bacterium belongs to the species *Streptococcus*. More preferably, the bacterium is selected from the group consisting of

*Streptococcus salivarius thermophilus* NGB-22D, deposited on 28 Feb. 2012 as CBS132067 at the Centraalbureau voor Schimmelcultures (Fungal Biodiversity Centre), Utrecht.

*Streptococcus salivarius thermophilus* DS65008, deposited on 18 Jun. 2013 as CBS135685 at the Centraalbureau voor Schimmelcultures (Fungal Biodiversity Centre), Utrecht.

The bacterium of the invention preferably produces a heteropolysaccharide as defined hereinbefore, i.e. that it is composed substantially of the monosaccharides glucose and galactose and rhamnose and N-acetylgalactosamine. The bacterium is capable of producing the preferred compositions of the heteropolysaccharide as defined in the first aspect of the invention. The bacterium of the invention is also capable of producing a heteropolysaccharide composed of the basic repeating unit as defined in the first aspect of the invention.

In a third aspect, the invention provides a process for the production of a fermented milk product comprising adding the heteropolysaccharide of the invention as defined in the first aspect of the invention. The effect of adding the heteropolysaccharide of the invention is that a highly viscous, stretchable and smooth texture fermented milk product is obtained compared to adding no heteropolysaccharide or compared to adding a heteropolysaccharide having a different composition.

In another embodiment, the invention provides a process for the production of a fermented milk product comprising adding the bacterium of the invention capable of producing the heteropolysaccharide as defined the second aspect of the invention. In this embodiment, the bacterium in situ produces the heteropolysaccharide in the process for the production of a fermented milk product which results in an improved texture and/or viscosity of the fermented milk product compared to adding no bacterium of the invention or compared to adding a bacterium capable of producing a polysaccharide having a different composition.

The fermented product may be any fermented milk product wherein an improved texture and/or viscosity is desired. The fermented milk product may be selected from, but is not limited to, a fermented product such as yoghurt, drink yoghurt, (low fat) cheese, kefir, buttermilk, sour cream, or soy yoghurt, and the like. Such food product may further comprise common ingredients for the preparation of desserts, such as fruits, chocolate chips or cereals for example, but also sweetened products or liquid chocolates. The food product may further comprise common food ingredients such as emulsifiers, gelling agents, stabilizers, sweeteners, and the like. The person skilled in the art knows how to prepare a food product using the (fermented) food from the present invention.

In a fourth aspect, the invention provides a process for the production of the heteropolysaccharide of the invention as defined in the first aspect of the invention. Preferably, in the process for the production of the heteropolysaccharide of the invention the bacterium of the invention as defined in the second aspect of the invention, is cultured in a culture medium under conditions conducive for the production of the heteropolysaccharide of the invention. The heteropolysaccharide of the invention may be collected from the fermentation broth which comprises the biomass of the bacterium, the heteropolysaccharide of the invention and other components using techniques known in the art.

In a fifth aspect the invention provides the use of the heteropolysaccharide of the invention as defined in the first aspect of the invention for improving the texture and/or viscosity of a fermented milk product. Preferably the fermented milk product is yogurt or cheese.

In a sixth aspect the invention provides the use of the bacterium of the invention as defined in the second aspect of the invention for improving the texture and/or viscosity of a fermented milk product.

MATERIALS AND METHODS

| Strains | | | |
|---|---|---|---|
| Strain | Code | Deposit number | Deposit date |
| Comparative Strains | | | |
| Streptococcus salivarius thermophilus | STV88 | Not deposited* | |
| Streptococcus salivarius thermophilus | 300E | CBS129458*** | 06-05-2011 |
| Streptococcus salivarius thermophilus | BLF5-1 | CBS132133*** | 13-03-2012 |
| Streptococcus thermophilus | ST144 | CCDM 144** | |
| Strains of the invention | | | |
| Streptococcus salivarius thermophilus | NGB-22D | CBS132067*** | 28-02-2012 |
| Streptococcus salivarius thermophilus | DS65008 | CBS135685*** | 18-06-2013 |

*Strain STV88 is a commercial strain and can be obtained from DSM Food Specialties B.V. in Delft, The Netherlands under the trade name DELVO ®-ADD 100-F.
**Streptococcus thermophilus ST144 was obtained from the Culture Collection of Dairy Microorganisms (Milcom), Sobeslavska 841, 39001 Tabor, Czech Republic
***Strains were deposited with the Centraalbureau voor Schimmelcultures (Fungal Biodiversity Centre), Uppsalalaan 8, 3584 CT Utrecht, the Netherlands on the indicated dates (deposit date) and received the corresponding Deposit Numbers.

Preparation of Fermented Milk Products

Commercial UHT semi-skimmed milk (Campina, The Netherlands) is supplemented with 2% (w/w) skimmed milk powder. Aliquots of 200 ml milk are pasteurized by heating the milk in a water bath for 15 min at 90° C., followed by 30 min at 85° C. After pasteurization the milk is quickly cooled to 4° C. using ice-water. The pasteurized milk is inoculated with $10^6$ cfu/ml (colony forming units/ml) of the various bacterial cultures and incubated at 42° C. until a pH of 4.6 is obtained. The pH of cultures was continuously monitored using a CINAC apparatus (Ysebaert, France). Simultaneously, for the purpose of Brookfield viscosity measurements 125 ml milk is fermented in an identical manner in cups (150 ml volume, diameter 5.5 cm).

The fermented milks thus obtained are cooled in ice water and stored at 4° C. until further analysis.

EPS Isolation from Fermented Milks.

40 mL of fermented milk was heated for 1 hour at 55° C. in a 50 mL tube to liberate the EPS. For precipitation of the protein 2.67 mL 60% (w/v) TCA was added and the solution was gently shaken for 1.5 hours at a temperature between 20 and 25° C. After centrifugation 30 minutes at 6300 g at a temperature of 4° C. the supernatant was quantitatively transferred to a 100 mL bottle and the pH was adjusted to 4.0 with 5 N sodium hydroxide (NaOH). The supernatant was quantitatively transferred into a 30 cm dialyse tube (4 SpectraPor membrane MWCO 12 000-14 000, Spectrum Laboratories Inc) and dialysed for about 16 hours (overnight) against tap water followed by dialysing 2 hours with reversed osmoses (RO) water. Before use the dialysis tube was boiled in a 2% sodium carbonate ($Na_2CO_3$) solution for 15 minutes and washed twice with RO water and boiled again with RO water for 15 minutes. The dialysis tubes were stored in RO water until use. The dialysed liquid was then quantitatively transferred to a plastic cup (the dialyse tube was washed twice with 5 mL RO water) and freeze dried during 2 days.

SEC-MALLS Analyses

The size exclusion chromatography (SEC) systems consisted of a TSK gel PWXL guard column, 6.0 mm×4.0 cm, TSK gel G6000 PWXL analytical column, 7.8 mm×30 cm, 13.0 μm and TSK gel G5000 PWXL analytical column, 7.8 mm×30 cm, 10 μm (TosoHaas) connected in series and thermostatted at 35° C. with a temperature control module (Waters).

The eluent was in-line vacuum degassed (1200 series, Agilent Technologies) and pumped (1200 series, Agilent Technologies) with a flow of 0.5 mL/min. Samples were placed in a thermally controlled sample holder at 10° C. and 200 μL was injected on the columns (model 231 Bio, Gilson).

Light scattering was measured at 632.8 nm at 15 angles between 32° and 144° (DAWN DSP-F, Wyatt Technologies). UV absorption was measured at 280 nm (CD-1595, Jasco) to detect protein.

Data collection and processing were performed using ASTRA V software (version 5.3.2.22, Wyatt Technologies). For normalization, the reference material bovine serum albumine (BSA) was used (M.W.=67000 Da). The eluent was 100 mM $NaNO_3$+0.02% $NaN_3$. Before use the eluent was filtered over a 0.20 μm filter and in line over a 0.025 μm filter which was placed between the pump and the injector. The freeze dried EPS sample was dissolved in eluent at a concentration of 25 mg/mL and filtered over a 0.20 μm filter before injection.

Analysis of Monosaccharides after Acid Hydrolyses of EPS
Acid Hydrolysis of Polysaccharide—

During the analysis with size exclusion chromatography (SEC) the polysaccharide peak was collected (between 29 and 31 min: 2 min×0.5 mL/min=1 mL). A stock solution of TFA (1 mL; 4 M) was added and the acid hydrolyses of the collected polysaccharide solution was carried out 75 min at 120° C. with 2 M trifluoro acetic acid (TFA) under nitrogen (N2). After hydrolyses the solution was dried overnight at room temperature under vacuum and dissolved in water (100 μL) and analysed by HPAEC-PAD.

HPAEC-PAD Analyses—

High Performance Anion Exchange Chromatography with Pulsed Amperometric Detection (HPAEC-PAD) on a gold electrode was used for the quantitative analyses of the monosaccharides rhamnose, galactosamine, arabinose, glucosamine, galactose, glucose, mannose, xylose, galacturonic acid and glucuronic acid. The analyses were performed with a 600E System controller pump (Waters) with a helium degassing unit and a model 400 EC detector (EG&G) using a VT-03 flow cell (Antec Leyden) and the settings for waveform B as described in the technical note 21 of Dionex. With a 717 autosampler (Waters), 20 μL of the sample was injected on a Carbopac PA-1, 250×4 mm (10-32), column (Dionex) thermostated at 30° C. The monosaccharides were eluted at a flow rate of 1.0 mL/min. The monosaccharides were eluted isocratic with 16 mM sodium hydroxide followed by the elution of the acid monosaccharides starting at 20 min with a linear gradient to 200 mM sodium hydroxide+ 500 mM sodium acetate in 20 minutes.

Data analysis was done with Chromeleon software version 6.80 (Dionex). Quantitative analyses were carried out using standard solutions (between 40 and 250 mg/L) of the monosaccharides (Sigma-Aldrich), which were subjected to the acid hydrolysis conditions.

Texture Analyses

The texture of the yoghurts was qualitatively assessed by manually stirring the yoghurt in a cup using a long plastic spoon. The thickness and gumminess of the sample was evaluated by the observed resistance during stirring. The long and short texture were evaluated by allowing a spoonful of yoghurt to flow from the spoon. A short yoghurt will drop from the spoon as a lump, whereas a long yoghurt will flow from the spoon while forming a thread.

EXAMPLES

Example 1

Characteristics of EPS Produced by S. thermophilus Strains

Fermented milks were made with different S. thermophilus strains and the EPS was isolated therefrom as described in the Materials and Methods. Table 1 summarizes the texture and thickening of the fermented milks as well as the sugar composition of the EPS and their molecular weight.

Strain BLFS-1 serves as a control since it gives a breakable and granular texture ("short"). Strain STV88 is a prior art strain and is known to give an averagely texturized, stretchable and smooth ("long") fermented in comparison with the control strain BLFS-1. Strain ST144 serves as a control since it has the same sugar composition as the strains of the invention but a much lower molecular weight. This strain also gives a short texture.

Strains NGB-22D and DS65008 are strains representing the invention producing a highly viscous, stretchable and smooth ("long") textured fermented milk product.

Analysis of the EPS shows that strain NGB-22D and DS65008 produce an EPS of which the combination of the sugar composition and the molecular weight is unique compared to the EPS of the comparative strains.

TABLE 1

Sugar composition of isolated EPS of the S. thermophilus yoghurts strains.

| | | | Strain | | | | |
| --- | --- | --- | --- | --- | --- | --- | --- |
| | | | Comparative strains | | | Strains of the invention | |
| | | | STV88 | DS63547 | BLF5-1 | ST144 | NGB-22D | DS65008 |
| MW (kDa) | | | 360 | 2700 | 490 | 26* | 790 | 600 |
| Texture | | | Long | | Short | Short | Long | Long |
| Thickening | | | ++ | 0 | | | +++ | +++ |
| Sugar Mole % | | Glc | 50 | 31 | 36 | 40 | 40 | 40 |
| Composition | | Gal | 49 | 36 | 57 | 25 | 22 | 23 |
| | | Rha | nd | nd | 25 | 18 | 16 | 17 |
| | | GalNAc | 1 | 33 | 2 | 17 | 22 | 20 |
| | Molaer | Glc | 1 | 1 | 1 | 2 | 2 | 2 |
| | ratio | Gal | 1 | 1 | 2 | 1 | 1 | 1 |
| | | Rha | — | — | 1 | 1 | 1 | 1 |
| | | GalNAc | — | 1 | — | 1 | 1 | 1 |

*Taken from Vaningelgem (2004) - Tables 3 and 4
Glc = glucose; Gal = galactose; Rha = rhamnose; GalNAc = N-acetylgalactosamine. Other monosaccharides are not included as their values were below the detection limit. ND = not detectable;

The invention claimed is:

1. A culture medium comprising a bacterium capable of producing a heteropolysaccharide composed of at least about 90%, based on dry matter, monosaccharides glucose and galactose and rhamnose and N-acetylgalactosamine, wherein the heteropolysaccharide has a molecular weight of 100 kDa to 10,000 kDa;

wherein the heteropolysaccharide comprises a repeating unit whereby the repeating unit is a pentasaccharide composed of the monosaccharides glucose and galactose and rhamnose and N-acetylgalactosamine, and wherein the pentasaccharide has the following composition:

glucose:galactose:rhamnose:N-acetylgalactosamine=2:1:1:1.

2. The culture medium comprising the bacterium according to claim 1 wherein the bacterium is a *Streptococcus salivarius thermophilus*.

3. The culture medium comprising the bacterium according to claim 2, wherein the bacterium is selected from the group consisting of

*Streptococcus salivarius thermophilus* NGB-22D, deposited on 28 Feb. 2012 as CBS132067 at the Centraalbureau voor Schimmelcultures (Fungal Biodiversity Centre), Utrecht and

*Streptococcus salivarius thermophilus* DS65008, deposited on 18 Jun. 2013 as CBS135685 at the Centraalbureau voor Schimmelcultures (Fungal Biodiversity Centre), Utrecht.

4. A process for production of a fermented milk product comprising adding a *Streptococcus salivarius thermophilus* bacterium capable of producing a heteropolysaccharide composed of at least about 90%, based on dry matter, monosaccharides glucose and galactose and rhamnose and N-acetylgalactosamine,
- wherein the heteropolysaccharide has a molecular weight of 100 kDa to 10,000 kDa;
- wherein the heteropolysaccharide comprises a repeating unit whereby the repeating unit is a pentasaccharide composed of the monosaccharides glucose and galactose and rhamnose and N-acetylgalactosamine, and
- wherein the pentasaccharide has the following composition:

glucose:galactose:rhamnose:N-acetylgalactosamine=2:1:1:1, to a milk product to a milk product and fermenting the milk product containing the bacterium.

5. The process according to claim 4 wherein the fermented milk product is selected from the group consisting of yoghurt and cheese.

6. A process for the production of a heteropolysaccharide composed of at least about 90%, based on dry matter, monosaccharides glucose and galactose and rhamnose and N-acetylgalactosamine,
- wherein the heteropolysaccharide has a molecular weight of 100 kDa to 10,000 kDa;
- wherein the heteropolysaccharide comprises a repeating unit whereby the repeating unit is a pentasaccharide composed of the monosaccharides glucose and galactose and rhamnose and N-acetylgalactosamine, and
- wherein the pentasaccharide has the following composition:

glucose:galactose:rhamnose:N-acetylgalactosamine=2:1:1:1, comprising culturing a *Streptococcus salivarius thermophilus* bacterium capable of producing said heteropolysaccharide under conditions conducive for the production of the heteropolysaccharide, and
recovering the heteropolysaccharide.

7. A fermented milk product comprising the heteropolysaccharide produced according to the process of claim 6, wherein the fermented milk product exhibits improved texture and/or viscosity compared to a fermented milk product comprising a different heteropolysaccharide.

8. The process according to claim 6, wherein the *Streptococcus salivarius thermophilus* bacterium is selected from the group consisting of
- *Streptococcus salivarius thermophilus* NGB-22D, deposited on 28 Feb. 2012 as CBS132067 at the Centraalbureau voor Schimmelcultures (Fungal Biodiversity Centre), Utrecht[H] and
- *Streptococcus salivarius thermophilus* DS65008, deposited on 18 Jun. 2013 as CBS135685 at the Centraalbureau voor Schimmelcultures (Fungal Biodiversity Centre), Utrecht.

9. A fermented milk product produced by the process according to claim 8, wherein the fermented milk product exhibits improved texture and/or viscosity compared to a fermented milk product comprising a bacterium that produces a different heteropolysaccharide.

\* \* \* \* \*